(12) United States Patent
Minezawa et al.

(10) Patent No.: US 9,068,487 B2
(45) Date of Patent: Jun. 30, 2015

(54) SELECTIVE CATALYTIC REDUCTION SYSTEM

(75) Inventors: Masanobu Minezawa, Fujisawa (JP); Yasuhisa Oomura, Fujisawa (JP); Shinichi Harada, Fujisawa (JP)

(73) Assignee: ISUZU MOTORS LIMITED, Tokyo (JP)

( * ) Notice: Subject to any disclaimer, the term of this patent is extended or adjusted under 35 U.S.C. 154(b) by 135 days.

(21) Appl. No.: 13/699,502

(22) PCT Filed: May 16, 2011

(86) PCT No.: PCT/JP2011/061210
§ 371 (c)(1),
(2), (4) Date: Nov. 21, 2012

(87) PCT Pub. No.: WO2011/148807
PCT Pub. Date: Dec. 1, 2011

(65) Prior Publication Data
US 2013/0067892 A1    Mar. 21, 2013

(30) Foreign Application Priority Data

May 25, 2010  (JP) .................. 2010-119711

(51) Int. Cl.
*F01N 3/10* (2006.01)
*F01N 9/00* (2006.01)
(Continued)

(52) U.S. Cl.
CPC ............. *F01N 9/00* (2013.01); *F01N 3/2066* (2013.01); *F01N 2560/026* (2013.01);
(Continued)

(58) Field of Classification Search
CPC ... F01N 3/2066; F01N 9/00; F01N 2560/026; F01N 2560/14; F01N 2560/20; F01N 2610/02; F02D 41/1461; F02D 41/1463; F02D 41/062; F02D 41/1494; G01N 33/0037; Y02T 10/24
USPC .................... 60/286, 295, 301, 303
See application file for complete search history.

(56) References Cited

U.S. PATENT DOCUMENTS 5,645,745 A * 7/1997 Hartwick et al. ............. 219/497
6,050,086 A * 4/2000 Ishizuka et al. ................ 60/274
(Continued)

FOREIGN PATENT DOCUMENTS

JP  9-184443    7/1997
JP  2000-235015  8/2000
(Continued)

OTHER PUBLICATIONS

International Search Report of Corresponding PCT Application PCT/JP2011/061210 mailed Jul. 26, 2011.
(Continued)

*Primary Examiner* — Thomas Denion
*Assistant Examiner* — Matthew T Largi
(74) *Attorney, Agent, or Firm* — Staas & Halsey LLP (57) ABSTRACT

A selective catalytic reduction system (SCR) that reduces a burden on a battery resulting from energization of a heater and a decrease in time during which an NOx concentration cannot be detected. The SCR system includes: an SCR device; a dosing valve; NOx sensors; an urea solution injection control unit; electric heaters for raising respective temperatures of the NOx sensors to a sensor operating temperature; and an energization permission unit that prohibits energization of the heaters at the time of a start of an engine and permits energization of the heaters when engine revolutions become equal to or exceed a preset energization permission threshold value and such state lasts for a period of time equal to or exceeding a preset stabilization wait time.

1 Claim, 5 Drawing Sheets

(51) Int. Cl.

| | | |
|---|---|---|
| *F01N 3/20* | (2006.01) | |
| *F02D 41/14* | (2006.01) | |
| *G01N 33/00* | (2006.01) | |
| *F02D 41/06* | (2006.01) | |

(52) U.S. Cl.
CPC ........ *F01N 2560/14* (2013.01); *F01N 2560/20* (2013.01); *F01N 2610/02* (2013.01); *F02D 41/062* (2013.01); *F02D 41/1461* (2013.01); *F02D 41/1463* (2013.01); *F02D 41/1494* (2013.01); *G01N 33/0037* (2013.01); *Y02T 10/24* (2013.01)

(56) References Cited

U.S. PATENT DOCUMENTS

| | | | | |
|---|---|---|---|---|
| 6,476,364 | B1 * | 11/2002 | Shimamura et al. | 219/494 |
| 7,418,957 | B2 * | 9/2008 | Abe | 123/697 |
| 7,654,077 | B2 * | 2/2010 | Zillmer et al. | 60/277 |
| 7,805,928 | B2 * | 10/2010 | Shouda et al. | 60/285 |
| 8,438,837 | B2 * | 5/2013 | Hermansson et al. | 60/286 |
| 2003/0213795 | A1 * | 11/2003 | Toyoda | 219/501 |

FOREIGN PATENT DOCUMENTS

| | | | | | |
|---|---|---|---|---|---|
| JP | 2000235015 | A | * | 8/2000 | ........... G01N 27/409 |
| JP | 2000-303826 | | | 10/2000 | |
| JP | 2008-144672 | | | 6/2008 | |
| JP | 2008144672 | A | * | 6/2008 | |
| JP | 2009-288082 | | | 12/2009 | |
| JP | 2009288082 | A | * | 12/2009 | |

OTHER PUBLICATIONS

Patent Abstracts of Japan, Publication No. 2009-288082, Published Dec. 10, 2009.
Patent Abstracts of Japan, Publication No. 2000-303826, Published Oct. 31, 2000.
Patent Abstracts of Japan, Publication No. 2000-235015, Published Aug. 29, 2000.
Patent Abstracts of Japan, Publication No. 09-184443, Published Jul. 15, 1997.
Patent Abstracts of Japan, Publication No. 2008-144672, Published Jun. 26, 2008.
Written Opinion of the International Searching Authority mailed Jul. 26, 2011 in corresponding International Application No. PCT/JP2011/061210.

* cited by examiner

SELECTIVE CATALYTIC REDUCTION SYSTEM

CROSS-REFERENCE TO RELATED APPLICATIONS

This application claims the benefit of Japanese Patent Application No. 2010-119711, filed on May 25, 2010, the contents of which is incorporated herein by reference, which serves as priority for PCT Application No. PCT/JP2011/061210, filed May 16, 2011.

TECHNICAL FILED

The present invention relates to a Selective Catalytic Reduction ("SCR") system that performs exhaust gas purification for a diesel vehicle, and an SCR system heater that enables reduction in burden on a battery resulting from energization of a heater, and a decrease in time during which an $NO_x$ concentration cannot be detected.

BACKGROUND ART

As an exhaust gas purification system for purifying $NO_x$ in an exhaust gas from a diesel engine, an SCR system using an SCR device has been developed.

The SCR system supplies urea solution to an exhaust gas upstream of the SCR device to generate ammonia using heat of the exhaust gas, and using the ammonia, reduces $NO_x$ on an SCR catalyst to purify $NO_x$ (see, for example, patent literature 1).

CITATION LIST

Patent Literature 1: Japanese Patent Laid-Open No. 2000-303826
Patent Literature 2: Japanese Patent Laid-Open No. 2009-288082
Injection of urea solution is controlled according to the $NO_x$ concentration in an exhaust gas. For that control, an $NO_x$ sensor is provided in an exhaust pipe.

The $NO_x$ sensor achieves a detection function at a sensor operating temperature at which a detection element is activated. Thus, when the $NO_x$ sensor is used to detect an $NO_x$ concentration, it is necessary to make current flow in an electric heater attached to the $NO_x$ sensor to heat the $NO_x$ sensor to the sensor operating temperature (see, for example, patent literature 2).

Figure 8:
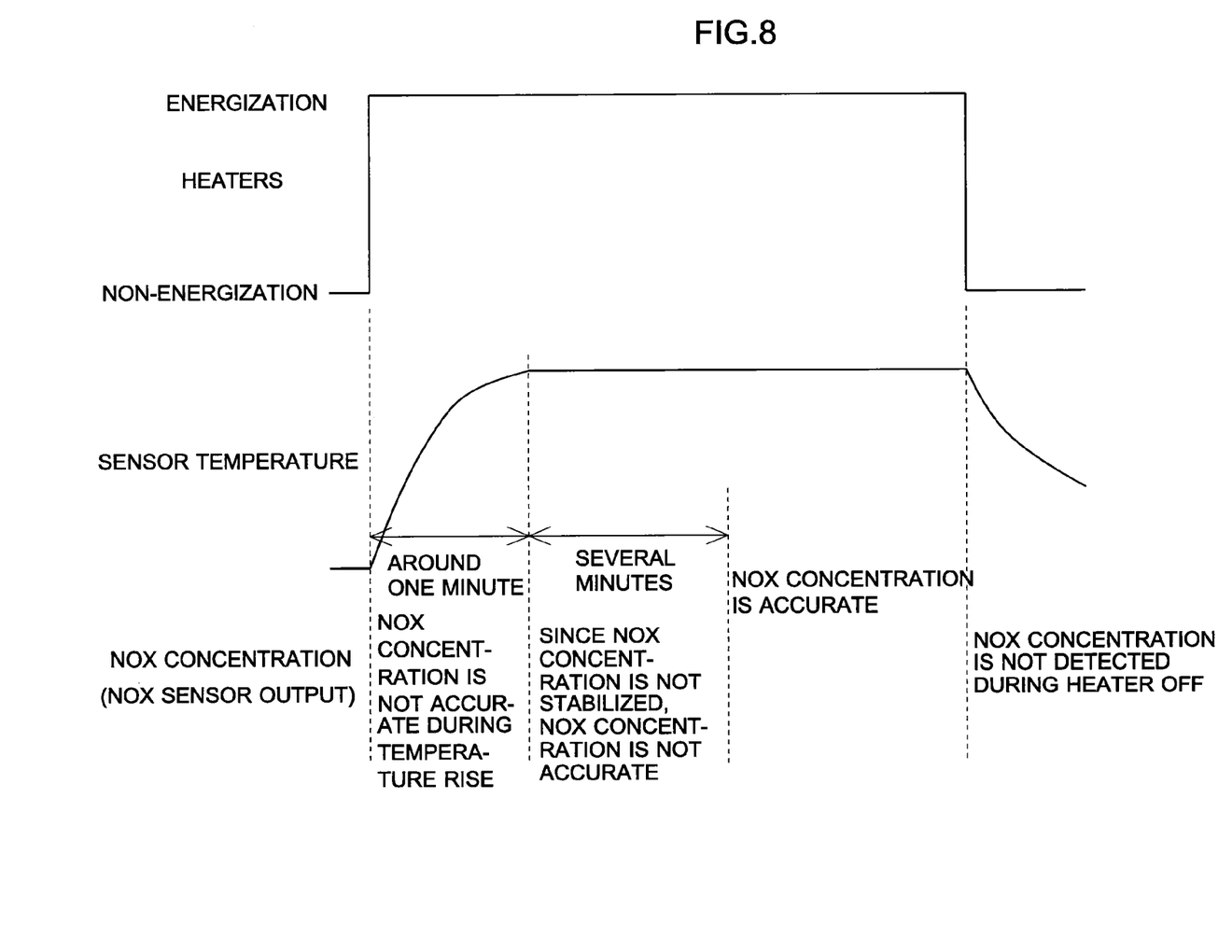
FIG. 8 is a timing chart indicating energization of a heater and change in temperature of an $NO_x$ sensor.

As illustrated in FIG. 8, if current starts to flow in the heater when the temperature of the $NO_x$ sensor is low, the temperature of the $NO_x$ sensor reaches the sensor operating temperature in around one minute, and if the current is stopped, the temperature of the $NO_x$ sensor is gradually lowered.

In order to raise the temperature of the $NO_x$ sensor to the sensor operating temperature in a short period of time, a heater that generates a large amount of heat is used for the heater. Thus, the heater significantly consumes power. The heater current is a large current of, for example, several hundreds of milliamperes. Where necessary, two $NO_x$ sensors may be installed in a vehicle, and in such case, a large current twice the aforementioned current flows in a total of heaters for the two $NO_x$ sensors.

Where an engine operates after the engine is sufficiently warmed up, power is supplied from an ACG (alternating current generator, i.e., alternator) and in addition, a battery is sufficiently charged, and thus, there is no problem if a large current flows in a heater. However, before a start of the engine or when the engine rotation is nearly stopped, no power is supplied from the ACG, and thus, when a large current flows in the heater, the battery may lack sufficient charge.

Furthermore, when a large current flows in the heater at the time of cranking performed by a starter motor during a start of the engine, if the amount of charge in the battery is insufficient, the battery voltage may be lowered to fall below an operation-guaranteed voltage for a control circuit for the engine, and as a result of the control circuit being stopped, the engine may fail to start.

Meanwhile, if energization of the heater is stopped (OFF), the temperature of the $NO_x$ sensor is gradually lowered to fall below the sensor operating temperature, and as a result, the $NO_x$ concentration cannot be detected. During the heater being off, the $NO_x$ concentration is not detected.

When the temperature of the $NO_x$ sensor is raised again, as illustrated in FIG. 8, the $NO_x$ concentration can be detected only after a wait of several minutes from the temperature of the $NO_x$ sensor reaching the sensor operating temperature. Thus, higher frequency of stoppage of energization of the heater extends the time during which the $NO_x$ concentration cannot be detected, and ideal exhaust gas purification cannot be expected.

SUMMARY OF THE INVENTION

Therefore, an object of the present invention is to solve the aforementioned problems and provide an SCR system that enables reduction in burden on a battery resulting from energization of a heater and a decrease in time during which an $NO_x$ concentration cannot be detected.

In order to achieve the above object, the present invention includes: a selective catalytic reduction device provided in an exhaust pipe for an engine; a dosing valve that injects urea solution on an upstream side of the selective catalytic reduction device; an $NO_x$ sensor that detects an $NO_x$ concentration in an exhaust gas; a urea solution injection control unit that controls the urea solution injection according to the $NO_x$ concentration detected by the $NO_x$ sensor; an electric heater for raising a temperature of the $NO_x$ sensor to a sensor operating temperature; and an energization permission unit that prohibits energization of the heater at the time of a start of the engine, and permits energization of the heater when an engine revolutions becomes equal to or exceeds a preset energization permission threshold value and such state lasts for a period of time equal to or exceeding a preset stabilization wait time.

The energization permission unit may prohibit energization of the heater when the engine revolutions becomes equal to or falls below a preset energization prohibition threshold value during operation of the engine and such state lasts for a period of time equal to or exceeding a preset recovery wait time.

Advantageous Effects of Invention

The present invention exerts excellent effects as follows.
(1) Burden on a battery resulting from energization of a heater is reduced.
(2) Time during which an $NO_x$ concentration cannot be detected can be decreased.

BRIEF DESCRIPTION OF DRAWINGS

FIG. 7 includes timings charts indicating a timing for prohibiting energization of heaters during engine operation.

DETAILED DESCRIPTION OF EMBODIMENTS

Preferred embodiments of the present invention will be described below with reference to the drawings.

Figure 1:
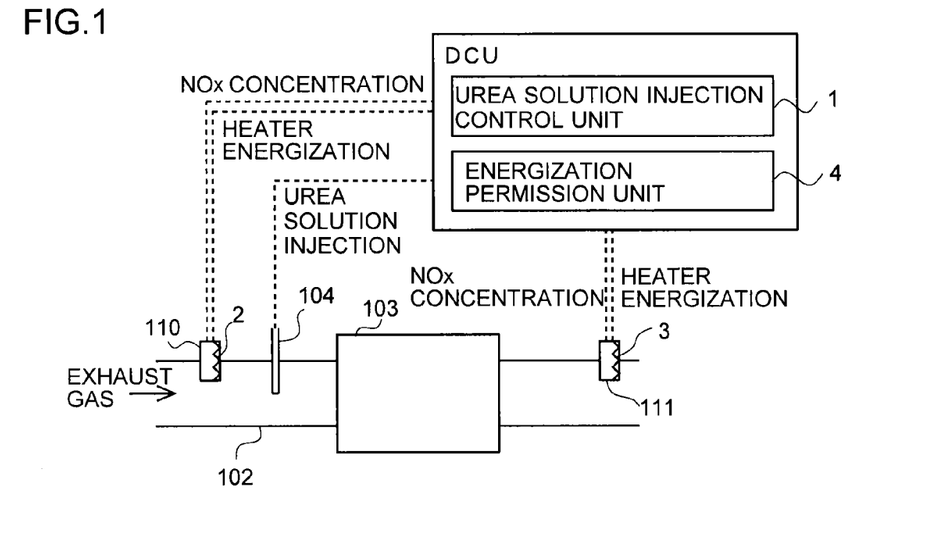
FIG. 1 is a diagram of a configuration of a main part of an SCR system representing an embodiment of the present invention.
Figure 2:
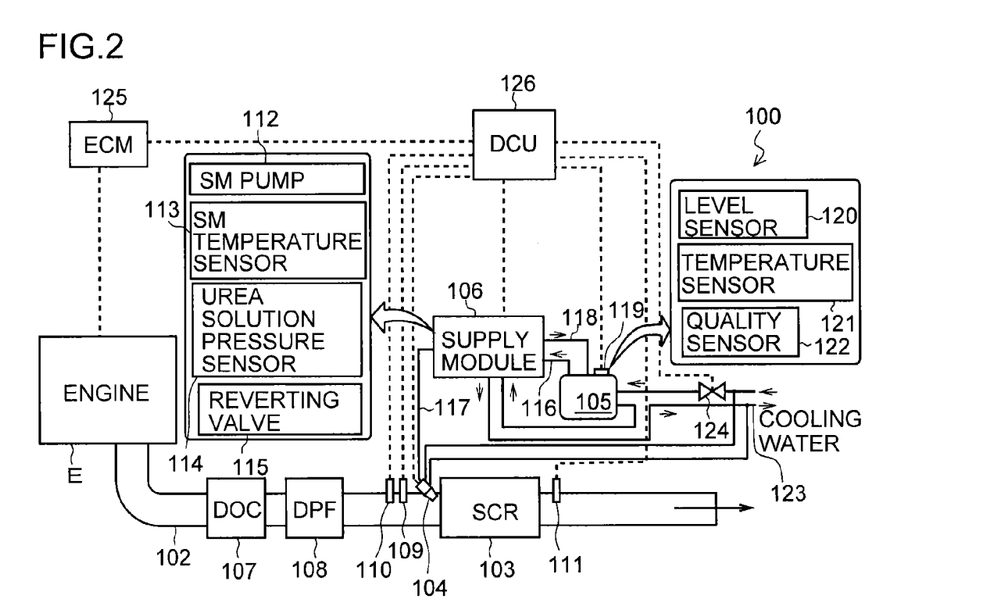
FIG. 2 is a configuration diagram illustrating an SCR system representing an embodiment of the present invention in detail.

As illustrated in FIGS. 1 and 2, an SCR system 100 according to the present invention includes: an SCR device 103 provided in an exhaust pipe 102 for an engine E; a dosing valve 104 that injects urea solution on the upstream side of the SCR device; $NO_x$ sensors 110 and 111 that each detect an $NO_x$ concentration in an exhaust gas; a urea solution injection control unit 1 that controls the urea solution injection according to the $NO_x$ concentrations detected by the $NO_x$ sensors 110 and 111; electric heaters 2 and 3 for raising respective temperatures of the $NO_x$ sensors 110 and 111 to a sensor operating temperature; and an energization permission unit 4 that prohibits energization of the heaters 2 and 3 at the time of a start of the engine, and permits energization of the heaters 2 and 3 when engine revolutions become equal to or exceed a preset energization permission threshold value v1 and such state lasts for a period of time equal to or exceeding a preset stabilization wait time t1.

Furthermore, the energization permission unit 4 is configured so as to prohibit energization of the heaters 2 and 3 when the engine revolutions become equal to or fall below a preset energization prohibition threshold value v2 during operation of the engine and such state lasts for a period of time equal to or exceeding a preset recovery wait time t2.

The urea solution injection control unit 1, which energizes the heaters 2 and 3 to raise respective temperatures of the $NO_x$ sensors 110 and 111 to the sensor operating temperature before reading $NO_x$ concentrations from respective signal lines for the $NO_x$ sensors 110 and 111, is configured so as to stop the energization of the heaters 2 and 3 when the energization permission unit 4 prohibits the energization and performs the energization of the heaters 2 and 3 only when the energization permission unit 4 permits the energization.

For more details, as illustrated in FIG. 2, the SCR system 100 mainly includes: the SCR device 103 provided in the exhaust pipe 102 for the engine E; the dosing valve (urea injection device or dosing module) 104 that injects urea solution on the upstream side of the SCR device 103 (upstream side of an exhaust gas); a urea tank 105 that stores urea solution; a supply module 106 that supplies urea solution stored in the urea tank 105 to the dosing valve 104 and a DCU (dosing control unit) 126 that controls, e.g., the dosing valve 104 and the supply module 106.

In the exhaust pipe 102 for the engine E, a DOC (diesel oxidation catalyst) 107, a DPF (diesel particulate filter) 108 and the SCR device 103 are sequentially disposed from the upstream side to the downstream side of an exhaust gas. The DOC 107 is provided to oxidize NO in an exhaust gas emitted from the engine E to $NO_2$ to control a ratio between NO and $NO_2$ in the exhaust gas for enhancement in denitration efficiency of the SCR device 103. Also, the DPF 108 is provided to collect PM (particulate matter) in the exhaust gas.

In the exhaust pipe 102 on the upstream side of the SCR device 103, the dosing valve 104 is provided. The dosing valve 104 has a structure in which a cylinder filled with high-pressure urea solution is provided with an injection orifice and a valving element occluding the injection orifice is attached to a plunger, and upon energization of a coil to pull up the plunger, the valving element is moved away from the injection orifice, whereby urea solution is injected. Upon the energization of the coil being stopped, the plunger is pulled down by means of an internal spring force so that the valving element occludes the injection orifice, whereby the injection of urea solution is stopped.

In the exhaust pipe 102 on the upstream side of the dosing valve 104, an exhaust temperature sensor 109 that measures a temperature of an exhaust gas at an entrance of the SCR device 103 (SCR entrance temperature) is provided. Also, on the upstream side of the SCR device 103 (here, the upstream side of the exhaust temperature sensor 109), the upstream-side $NO_x$ sensor 110 that detects an $NO_x$ concentration on the upstream side of the SCR device 103 is provided, and on the downstream side of the SCR device 103, the downstream-side $NO_x$ sensor 111 that detects a $NO_x$ concentration on the downstream side of the SCR device 103 is provided.

The supply module 106 includes: an SM pump 112 that pressure-feeds urea solution; an SM temperature sensor 113 that measures a temperature of the supply module 106 (temperature of urea solution flowing in the supply module 106); a urea solution pressure sensor 114 that measures a pressure of the urea solution in the supply module 106 (pressure on the discharge side of the SM pump 112); and a reverting valve 115 that switches between supply of urea solution from the urea tank 105 to the dosing valve 104 and return of urea solution in the dosing valve 104 to the urea tank 105 by switching between flow passages of urea solution. Here, arrangement is made so that when the reverting valve 115 is on, the urea solution from the urea tank 105 is supplied to the dosing valve 104 and when the reverting valve 115 is off, the urea solution in the dosing valve 104 is returned to the urea tank 105.

When switching of the reverting valve 115 is made so that urea solution is supplied to the dosing valve 104, the supply module 106 sucks up urea solution in the urea tank 105 through a liquid feed line (suction line) 116 via the SM pump 112 and supplied to the dosing valve 104 through a pressure-feed line (pressure line) 117 and extra urea solution is returned to the urea tank 105 through a collection line (return line) 118.

In the urea tank 105, an SCR sensor 119 is provided. The SCR sensor 119 includes: a level sensor 120 that measures a liquid level of urea solution in the urea tank 105; a temperature sensor 121 that measures a temperature of the urea solution in the urea tank 105; and a product quality sensor 122 that measures a product quality of the urea solution in the urea tank 105. The product quality sensor 122 is configured to detect a concentration of urea solution and/or whether a heterogeneous mixture is mixed in the urea solution, based on, for example, an ultrasound propagation speed and/or electrical conductivity to detect a product quality of the urea solution in the urea tank 105.

A cooling line 123 that circulates cooling water for cooling the engine E is connected to the urea tank 105 and the supply module 106. The cooling line 123 runs through the inside of the urea tank 105 for heat exchange between cooling water flowing in the cooling line 123 and urea solution in the urea tank 105. Likewise, the cooling line 123 runs through the inside of the supply module 106 for heat exchange between the cooling water flowing in the cooling line 123 and urea solution in the supply module 106.

In the cooling line 123, a tank heater valve (coolant valve) 124 that provides a switch for whether or not cooling water is supplied to the urea tank 105 and the supply module 106 is provided. Although the cooling line 123 is connected also to the dosing valve 104, arrangement is made so that cooling water is supplied to the dosing valve 104 irrespective of whether the tank heater valve 124 is opened or closed. The cooling line 123 is disposed along the liquid feed line 116, the pressure-feed line 117 and the collection line 118 through which urea solution passes, which is, however, not illustrated in FIG. 2 for simplification of the Figure.

Figure 3:
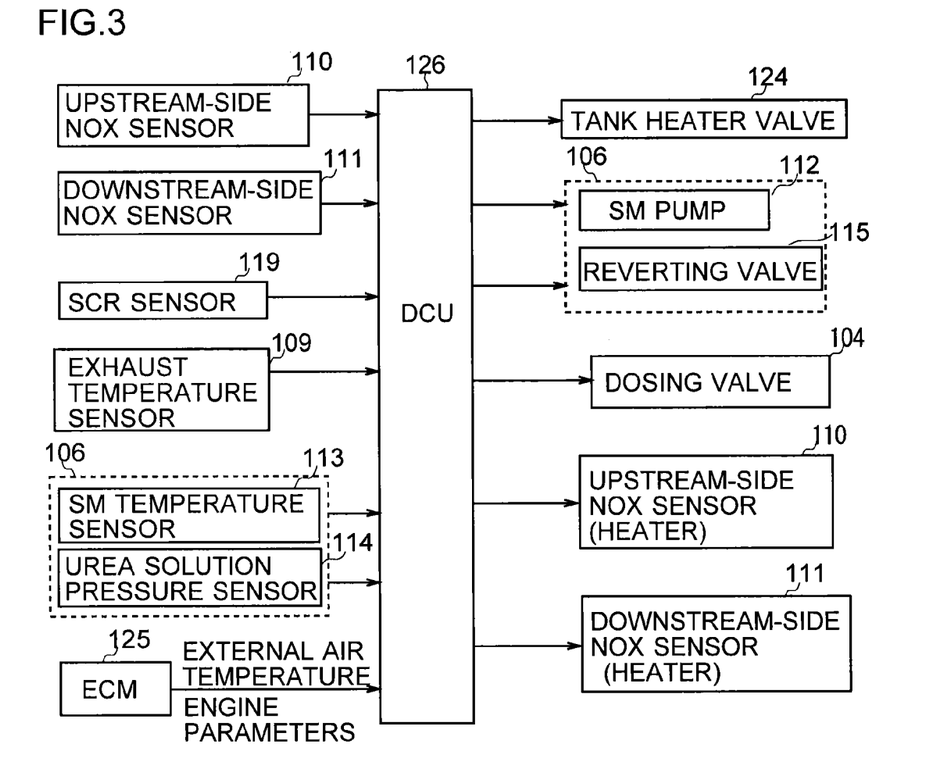
FIG. 3 is a diagram of an input/output configuration of the SCR system in FIG. 1.

FIG. 3 is a diagram of an input/output configuration of the DCU 126.

As illustrated in FIG. 3, input signal lines from the upstream-side $NO_x$ sensor 110, the downstream-side $NO_x$ sensor 111, the SCR sensor 119 (the level sensor 120, the temperature sensor 121 and the product quality sensor 122), the exhaust temperature sensor 109, the SM temperature sensor 113 and the urea solution pressure sensor 114 in the supply module 106 and an ECM (engine control module) 125 that controls the engine E are connected to the DCU 126. From the ECM 125, signals for an external air temperature and engine parameters (e.g., engine revolutions) are input.

Also, output signal lines to the tank heater valve 124, the SM pump 112 and the reverting valve 115 in the supply module 106, the dosing valve 104, the heater 2 for the upstream side $NO_x$ sensor 110 and the heater 3 for the downstream side $NO_x$ sensor 111 are connected to the DCU 126. Here, input/output of signals between the DCU 126 and the respective members may be made via the individual signal lines or a CAN (controller area network).

The urea solution injection control unit 1 in the DCU 126 is configured to estimate a quantity of $NO_x$ in an exhaust gas based on the signals for the parameters for the engine from the ECM 125 and a temperature of the exhaust gas from the exhaust temperature sensor 109 and determine a quantity of urea solution to be injected from the dosing valve 104 based on the estimated quantity of $NO_x$ in the exhaust gas, and furthermore, when the determined quantity of urea solution is injected via the dosing valve 104, controls the dosing valve 104 based on a value detected by the upstream-side $NO_x$ sensor 110 to adjust the quantity of urea solution injected via the dosing valve 104.

An operation of the SCR system 100 according to the present invention will be described below.

Figure 4:
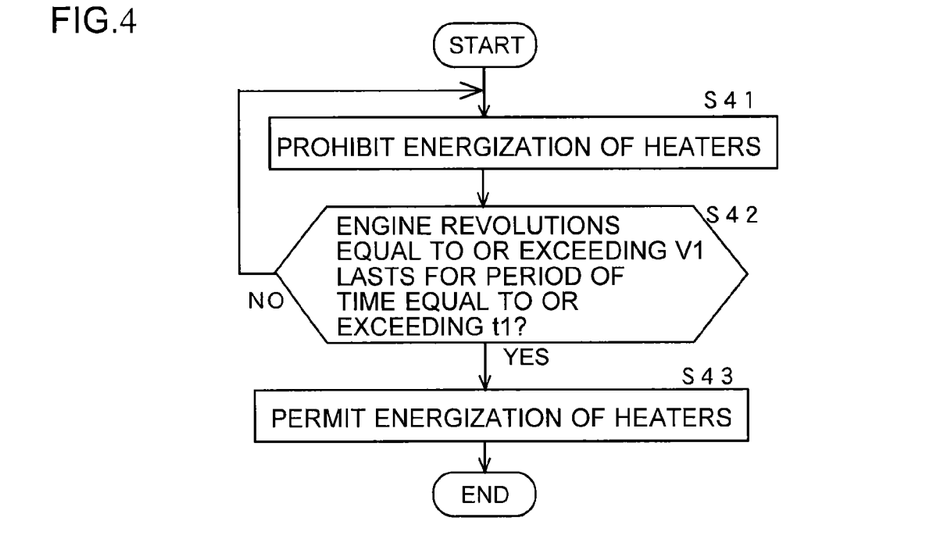
FIG. 4 is a flowchart illustrating a procedure for permitting energization of heaters in the energization permission unit in FIG. 1.

The procedure in FIG. 4 is executed at the time of a start of the engine. As illustrated in FIG. 4, in step S41, the energization permission unit 4 prohibits energization of the heaters 2 and 3 when the engine is started. Next, in step S42, the energization permission unit 4 determines whether or not a state in which the engine revolutions is equal to or exceeds the energization permission threshold value v1 lasts for a period of time equal to or exceeding the stabilization wait time t1. If the result of the determination is NO, the procedure returns to step S41. In other word, the prohibition of energization continues until a period of time equal to or exceeding the stabilization wait time t1 elapses in a state in which the engine revolutions are equal to or exceed the energization permission threshold value v1. If the result of the determination is YES, the procedure proceeds to step S43.

In step S43, the energization permission unit 4 permits energization of the heaters 2 and 3.

Figure 5:
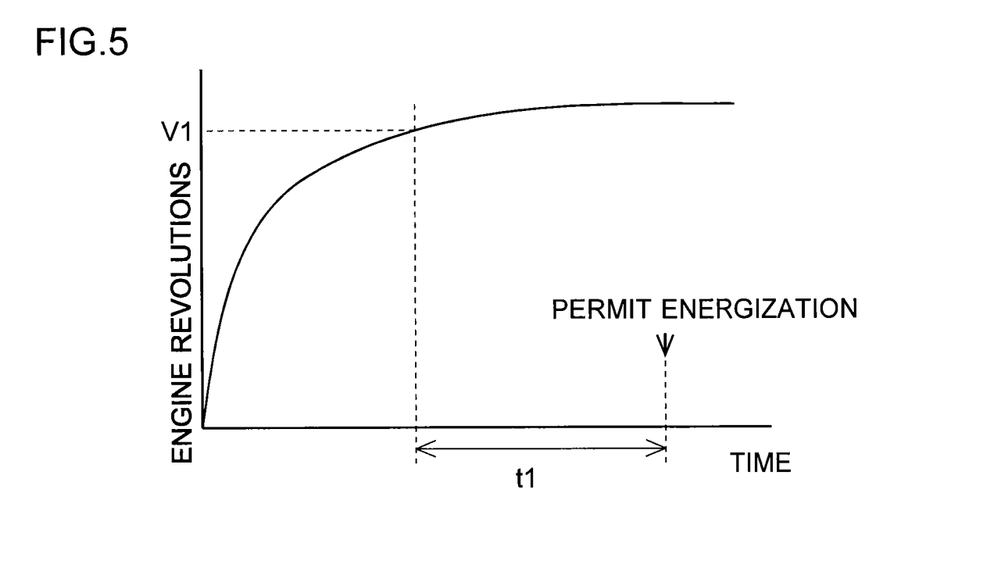
FIG. 5 is a timing chart indicating a timing for energization of heaters at the time of an engine start.

As a result of execution of the procedure in FIG. 4, energization of the heaters 2 and 3 is started at the timing in FIG. 5. In other words, when the engine revolutions become equal to or exceed the energization permission threshold value v1 and a period of time equal to or exceeding the stabilization wait time t1 has elapsed, energization of the heaters 2 and 3 is started. When current starts to flow in the heaters 2 and 3, as already described, the respective temperatures of the $NO_x$ sensors 110 and 111 reach the sensor operating temperature in around one minute, enabling the urea solution injection control unit 1 to read the $NO_x$ concentrations and control the urea solution injection according to the $NO_x$ concentrations.

As described above, the energization permission unit 4 prohibits energization of the heaters 2 and 3 at the time of a start of the engine, and permits energization of the heaters 2 and 3 when the engine revolutions become equal to or exceed the energization permission threshold value v1 and such state lasts for a period of time equal to or exceeding the stabilization wait time t1. Accordingly, current flows in the heaters 2 and 3 after supply of power from the ACG becomes possible, and thus, there is no fear of battery falling short of charge.

It is preferable that the energization permission threshold value v1 be set to an idle speed or a rotation speed somewhat lower than the idle speed. This is because sufficient activation of the ACG is ensured when a certain period of time has elapsed after the engine revolutions become the idle speed.

Since the stabilization wait time t1 differs depending on the type of the vehicle, it is preferable to determine the stabilization wait time t1 by finding out a period of time in which the ACG is stabilized, by experiment. For example, if the ACG is stabilized after lapse of two or three seconds from the engine revolutions becoming the idle speed, the stabilization wait time t1 is set to two or three seconds. It is preferable to set the stabilization wait time t1 to a short period of time because as the stabilization wait time t1 is set to a shorter period of time, the $NO_x$ concentration detection can be started earlier.

Figure 6:
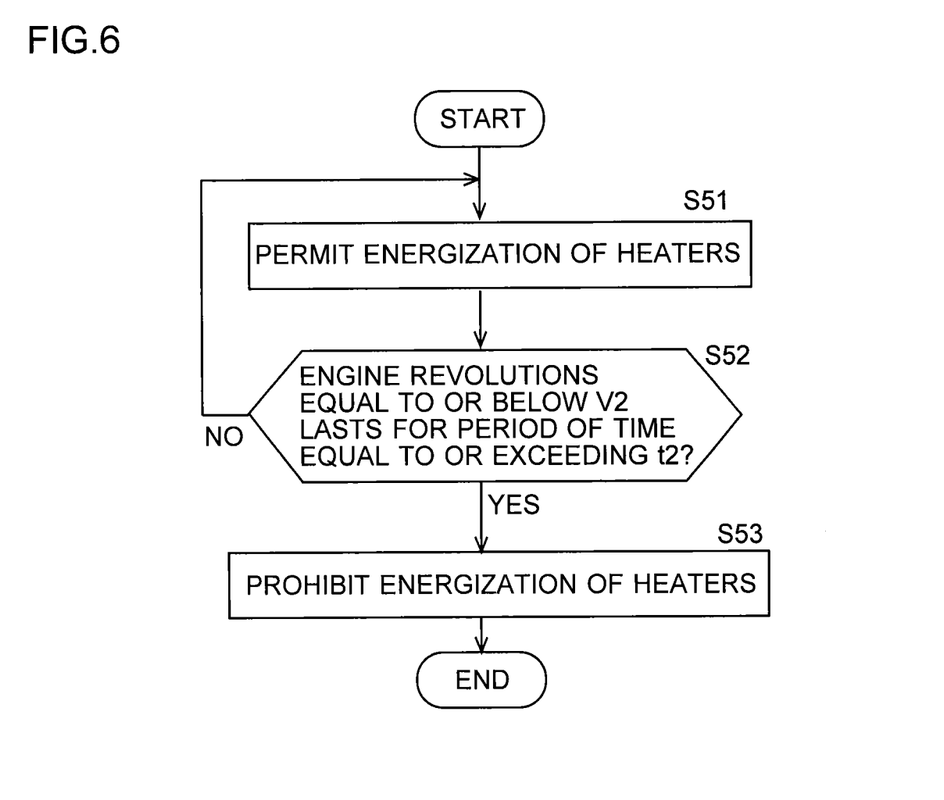
FIG. 6 is a flowchart illustrating a procedure for prohibiting energization of heaters in the energization permission unit in FIG. 1.

Next, during operation of the engine, the procedure in FIG. 6 is executed. As illustrated in FIG. 6, in step S51, the energization permission unit 4 permits energization of the heaters 2 and 3 because the engine is operating. Next, in step S52, the energization permission unit 4 determines whether a state in which the engine revolutions are equal to or below the energization prohibition threshold value v2 lasts for a period of time equal to or exceeding the recovery wait time t2. If the result of determination is NO, the procedure returns to step S51. In other words, the permission of the energization is continued unless a period of time equal to or exceeding the recovery wait time t2 elapses in a state in which the engine revolutions is equal to or below the energization prohibition threshold value v2. If the result of determination is YES, the procedure proceeds to step S53.

In step S53, the energization permission unit 4 prohibits energization of the heaters 2 and 3.

Figure 7A:
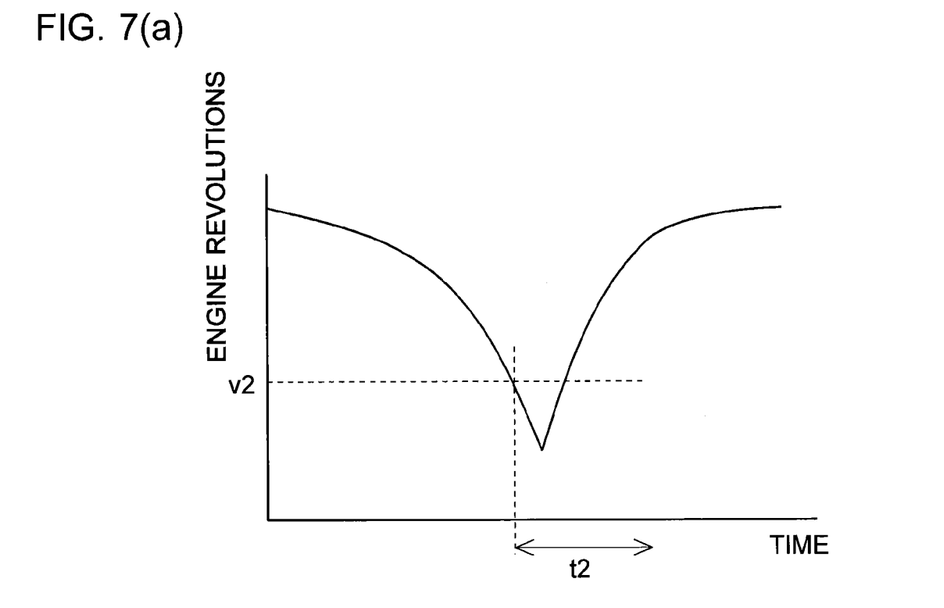
FIG. 7(a) indicates a case where the energization is not prohibited, and FIG. 7(b) indicates a case where the energization is prohibited.
Figure 7B:
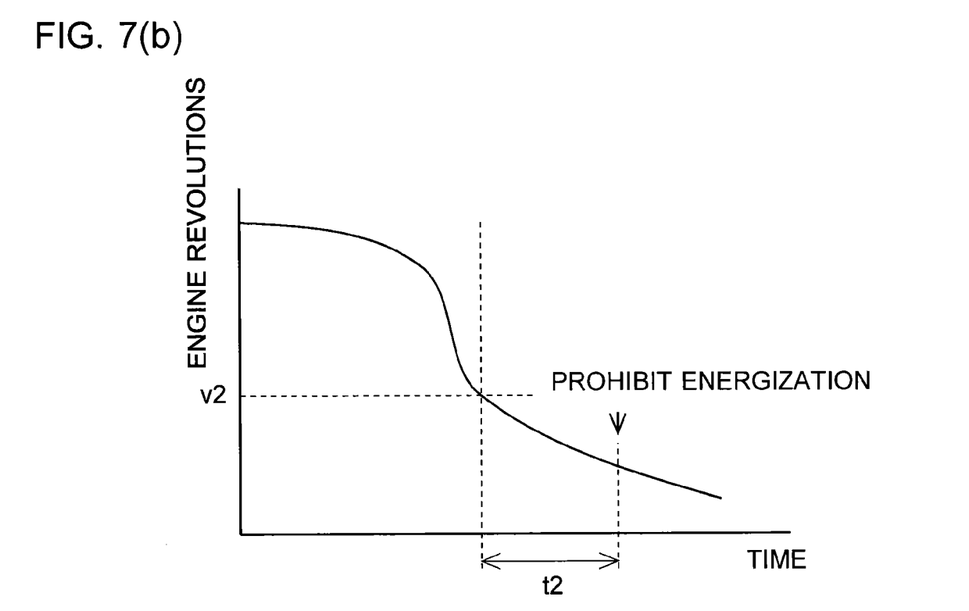

By the execution of the procedure in FIG. 6, the energization of the heaters 2 and 3 is continued or stopped at the timing indicated in FIG. 7(a) or 7(b), respectively. In other words, as illustrated in FIG. 7(a), it is assumed that after the engine revolutions fall to be equal to or below the energization prohibition threshold value v2 and before lapse of the recovery wait time t2, the engine revolutions rise and exceed the energization prohibition threshold value v2. In such case, the energization of the heaters 2 and 3 remains permitted and thus is continued. Meanwhile, as illustrated in FIG. 7(b), if the engine revolutions fall to be equal to or below the energization prohibition threshold value v2 and then such state lasts for the recovery wait time t2, the energization of the heaters 2 and 3 is prohibited and thus stopped.

As described above, the energization permission unit 4 prohibits energization of the heaters 2 and 3 when the engine revolutions become equal to or fall below the energization prohibition threshold value v2 during operation of the engine and such state lasts for a period of time equal to or exceeding the recovery wait time t2. Accordingly, until a lapse of the recovery wait time t2, the energization of the heaters 2 and 3 is permitted, a state in which the $NO_x$ concentrations can be detected by the upstream-side $NO_x$ sensor 110 and the downstream-side $NO_x$ sensor 111 is maintained. This is because even if almost no power from the ACG can be supplied, the battery is sufficiently charged by the operation of the engine up until immediately before and can respond to the demand for a large current within a period of time before lapse of the recovery wait time t2.

If the engine revolutions exceed the energization prohibition threshold value v2 before a lapse of the recovery wait time t2, supply of power from the ACG becomes possible again, and thus, the energization of the heaters 2 and 3 remains permitted.

Accordingly, a frequency of stoppage of the energization of the heaters 2 and 3 becomes low. As a result, the time during the $NO_x$ concentrations cannot be detected is reduced, allowing the urea solution injection to be properly controlled by the urea solution injection control unit 1, and thus, ideal exhaust gas purification can be expected.

It is preferable that the energization prohibition threshold value v2 be set to a value close to that for stoppage of the engine, that is, the engine revolutions=0. Since the recovery wait time t2 differs depending on the type of the vehicle, it is preferable to determine the recovery wait time t2 by finding out a period of time in which the battery falls short of charge to respond to the large current, by experiment.

The invention claimed is:

1. A selective catalytic reduction system comprising:
   a selective catalytic reduction device provided in an exhaust pipe for an engine;
   a dosing valve that injects urea solution into exhaust gas in the exhaust pipe on an upstream side of the selective catalytic reduction device;
   an $NO_x$ sensor that detects an $NO_x$ concentration in the exhaust gas;
   an electric heater for raising a temperature of the $NO_x$ sensor to a sensor operating temperature; and
   a dosing control device configured to—
   prohibit energization of the heater at a time of a start of the engine,
   permit the energization of the heater when engine revolutions become equal to or higher than a preset energization permission threshold value,
   wherein the energization of the heater is permitted to continue for a period of time equal to or exceeding a preset stabilization wait time, and
   wherein the preset stabilization wait time is a time from when the engine revolutions become equal to or higher than the preset energization permission threshold value to when supply of power from an alternating current generator becomes stabilized, and
   prohibit the energization of the heater when the engine revolutions become equal to or fall below a preset energization prohibition threshold value that is larger than 0, and
   permit the energization of the heater to continue for a period of time equal to or exceeding a preset recovery wait time during operation of the engine,
   wherein the energization of the heater continues when the engine revolutions become equal to or fall below the preset energization prohibition threshold value and the engine revolutions rise and exceed the preset energization prohibition threshold value before the energization is permitted to continue for a period of time equal to or exceeding the preset recovery wait time during operation of the engine, and
   wherein the preset recovery wait time is a time from when the engine revolutions become equal to or fall below the energization prohibition threshold value to when supply of power from a battery becomes unstabilized.

* * * * *